US012678082B2

(12) United States Patent
Wolfrum et al.

(10) Patent No.: US 12,678,082 B2
(45) Date of Patent: Jul. 14, 2026

(54) SUBSTRATE FOR AN IMPLANTABLE MICROELECTRODE, ELECTRODE ELEMENT, AND ELECTRODE SYSTEM AND ITS MANUFACTURING METHOD

(71) Applicant: NTT Research, Inc., Sunnyvale, CA (US)

(72) Inventors: Bernhard Wolfrum, Munich (DE); Tetsuhiko Teshima, Munich (DE); Lukas Hiendlmeier, Rinkam (DE); Francisco Zurita, Munich (DE)

(73) Assignee: NTT Research, Inc., Sunnyvale, CA (US)

( * ) Notice: Subject to any disclaimer, the term of this patent is extended or adjusted under 35 U.S.C. 154(b) by 172 days.

(21) Appl. No.: 18/845,326

(22) PCT Filed: Mar. 14, 2022

(86) PCT No.: PCT/EP2022/056518
§ 371 (c)(1),
(2) Date: Sep. 9, 2024

(87) PCT Pub. No.: WO2023/174508
PCT Pub. Date: Sep. 21, 2023

(65) Prior Publication Data
US 2025/0176888 A1 Jun. 5, 2025

(51) Int. Cl.
*A61B 5/268* (2021.01)

(52) U.S. Cl.
CPC ...... *A61B 5/268* (2021.01); *A61B 2562/0209* (2013.01); *A61B 2562/028* (2013.01); *A61B 2562/125* (2013.01)

(58) Field of Classification Search
CPC ... A61B 5/25; A61B 5/268; A61B 2562/0209; A61B 2562/028; A61B 2562/125; A61N 1/05; A61N 1/0556
See application file for complete search history.

(56) References Cited

U.S. PATENT DOCUMENTS

| 5,362,420 | A | 11/1994 | Itoh et al. |
| 2003/0099682 | A1 | 5/2003 | Moussy et al. |
| 2006/0182788 | A1 | 8/2006 | Singh et al. |

FOREIGN PATENT DOCUMENTS

| CN | 111657937 A | * | 9/2020 | .............. C23C 14/10 |
| WO | WO-2019053947 A1 | * | 3/2019 | ............... H05K 3/20 |

OTHER PUBLICATIONS

Written Opinion and International Search Report of the International Searching Authority in PCT/EP2022/056518 dated Sep. 21, 2023, 10 pages.

* cited by examiner

*Primary Examiner* — Eun Hwa Kim
(74) *Attorney, Agent, or Firm* — CipherLaw

(57) ABSTRACT

The present disclosure provides a substrate for an implantable microelectrode for being implanted into tissues or brought into contact with a single cell. The substrate comprises a first layer and a second layer deposited on at least a part of a first surface of the first layer. The first layer is based on a first mixture comprising a first photoinitiator and a first component with a first functional group. The second layer is based on a second mixture comprising a second photoinitiator, a second component that is an acid with a second functional group, a base to neutralize the second component, and a third component with third and fourth functional groups. The first and second components are photo-polymerizable, and the third component can cross-link the second component. A swelling capacity of the first layer is smaller than a swelling capacity of the second layer.

30 Claims, 9 Drawing Sheets

A
1-1
2
2
z
y
x
1
1-2
(a)
A
1-1
2
2
2
1
1-2
(b)
<u>Fig. 1</u>
2
z
y
x
$l_1, l_2$
$w_1, w_2$
(a)
2
2
2
$l_2$
$l_2$
$l_2$
$l_1, l_2$
$w_1, w_2$
(b)
<u>Fig. 2</u>
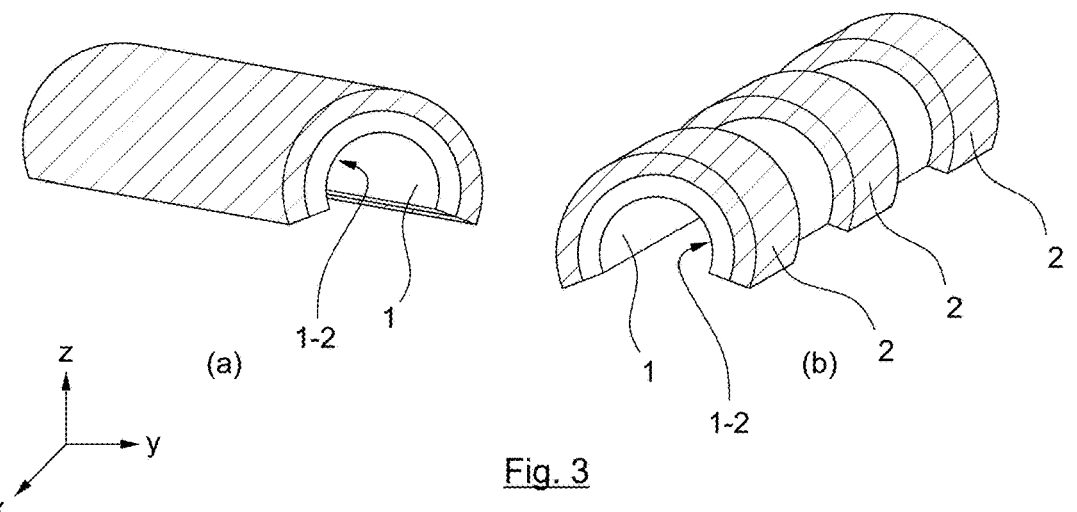
1-2
1
(a)
z
y
x
1
1-2
2
2
2
(b)
<u>Fig. 3</u>

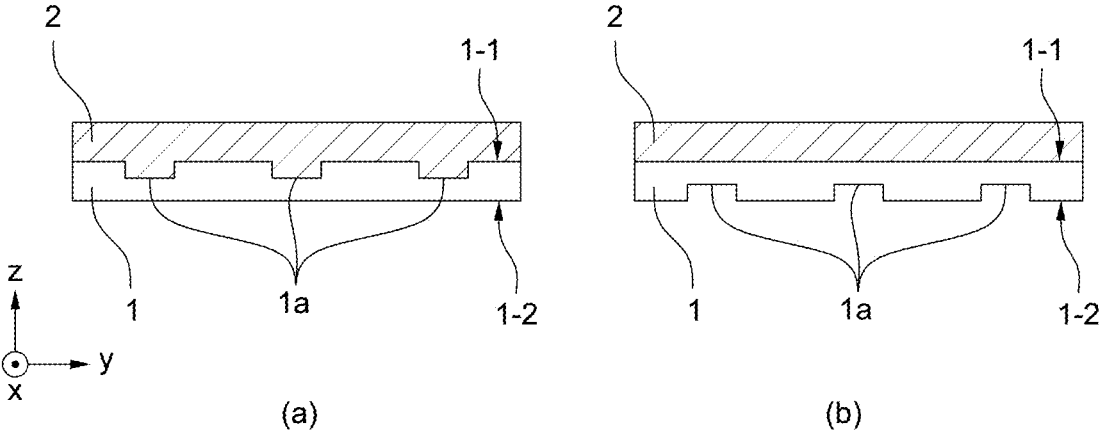
(a)                                        (b)
<u>Fig. 8</u>
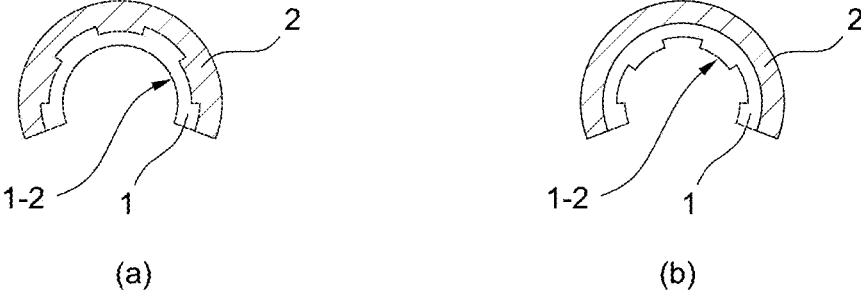
(a)                                        (b)
<u>Fig. 9</u>

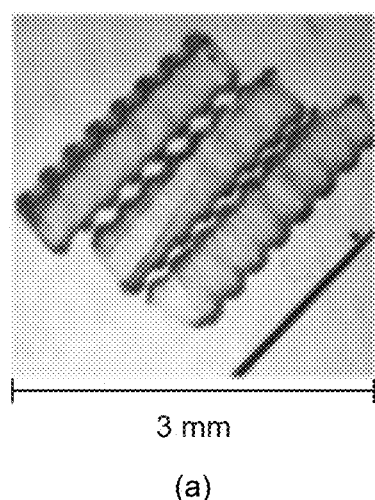
(a)
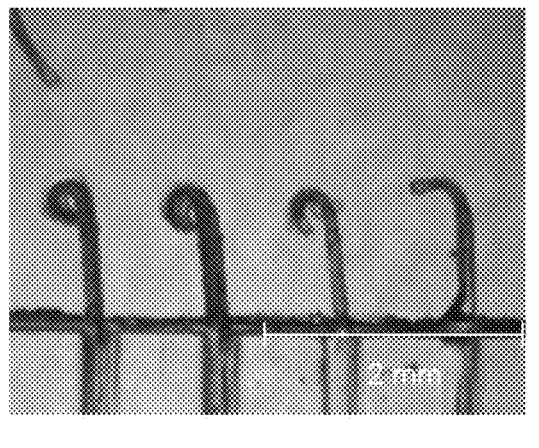
(b)
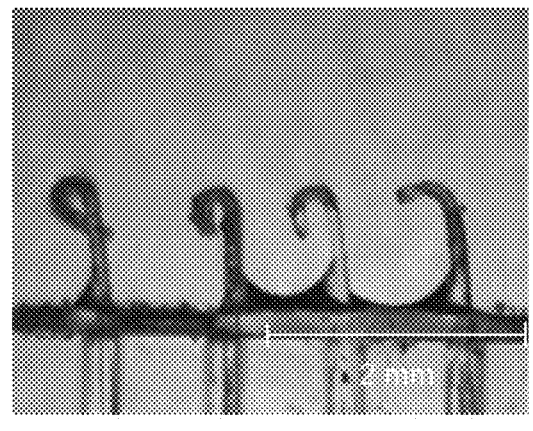
(c)
Fig. 10
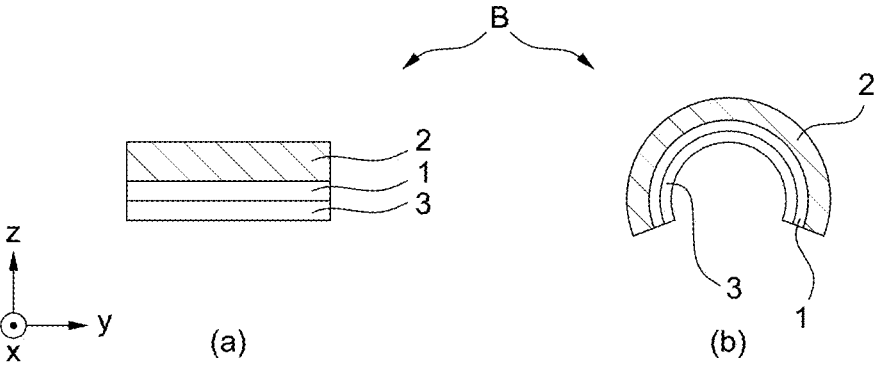
(a)
(b)
Fig. 11

<u>Fig. 13</u>

SUBSTRATE FOR AN IMPLANTABLE MICROELECTRODE, ELECTRODE ELEMENT, AND ELECTRODE SYSTEM AND ITS MANUFACTURING METHOD

TECHNICAL FIELD

The present disclosure relates to a substrate for an implantable microelectrode for being implanted into tissues such as a nerve or for being brought into contact with a single cell, in order to apply and/or record an electrical signal to and/or from the tissues or the single cell, The present disclosure further relates to an electrode element including the substrate and an electrode system including the electrode element. The substrate for an implantable microelectrode is able to curve itself, or more specifically, bend or fold itself, when contacting liquid including water molecules. The present disclosure further relates to methods for manufacturing the substrate, the electrode element, and the electrode system.

BACKGROUND

In current practice, implantable microelectrodes are used for neuroscience, for alleviating symptoms of neurological diseases, such as Parkinson's disease or epilepsy, or for restoring body functions after injury. Implantable microelectrodes are brought into the body of the patient via surgery and are used for recording from or stimulating the neural target tissue and nerves. Examples for implantable microelectrodes are stimulation electrodes that are used for deep brain stimulation. Other examples are cuff electrodes used for interfacing nerves and electrodes used for electrocorticography.

US2021/0270764 A1 discloses a microelectrode having a layered structure, including a layer containing a polymer compound having an aromatic ring (polymer compound layer) and a layer containing a conductive material (conductive layer), wherein a thickness of the polymer compound layer is 10 to 900 nm, a thickness of the conductive layer is 0.3 to 10 nm, and the microelectrode has a three-dimensional curved shape.

Such a microelectrode having a small dimension (nano- and micro-meter range) would be generally difficult to handle during an operation, for example when implanting the microelectrode into a tissue. A further challenge may be accurate fabrications of such three-dimensional structures of the microelectrode.

SUMMARY OF INVENTION

The technical problem to be solved may be formulated to provide a substrate for an implantable microelectrode and an electrode element/system including the substrate, which provides a stable, reliable, and controlled structure and may realize more accurate handling by a user.

A substrate for an implantable microelectrode according to the present disclosure comprises a first layer, or flexible non-swelling base layer, and a second layer or swelling layer being deposited on at least a part of a first surface of the first layer. The substrate is preferably a film or a flexible polymer compound(s) for forming and/or mounting an implantable microelectrode thereon. The implantable microelectrode may be for example a cuff electrode that is able to interface nerves with a diameter of about 50 to 500 μm. During implantation, the mechanical actuation of the implantable microelectrode according to the present disclosure can be initiated by an external stimulus, i.e. contacting liquid comprising water, which may allow the implantable microelectrode to deform and curve, bend, or fold itself around e.g. a nerve for forming a close and stable interface with the biological tissue. The implantable microelectrode may have a small area being electrically conductive for contacting a biological sample, and the area may be in the micrometer or millimeter range. The implantable microelectrode may be used, for example, for recording signals from the nerve tissue in the mV range or V range, or for stimulation of the nerve tissue with current pulses in the μA to mA range or with voltage pulses in the mV or V range.

Each of the first layer and the second layer extends in the x-direction and in the y-direction and/or in the xy-plane, and the first layer and the second layer are stacked in the z-direction. The x-, y-, z-axes and/or directions are of the three-dimensional rectangular coordinate system, which are orthogonal to each other. The direction, into which the layers (1, 2) are stacked, is the z-direction. The first layer and the second layer overlap each other in the z-direction. Therein, the first layer is based on a first mixture and/or the first layer is obtained by photo-polymerization (and/or curing) of a first mixture. The photopolymerization is a light-induced reaction, which converts a liquid mixture of one or more monomers and/or oligomers and/or polymers into a solid and/or hardened polymer. The reaction may require the use of an appropriate photoinitiator, which is a light sensitive molecule that produces active species or radicals upon irradiation with UV, visible, or infrared light. The first mixture comprises a first photoinitiator and a first component comprising at least one of a first monomer or a first oligomer or a first polymer, wherein the first monomer or the first oligomer or the first co-polymer comprises a first functional group. A monomer in general comprises a single unit of a certain chemical compound. An oligomer comprises more than one unit of the same or structurally similar chemical compounds, i.e. a number of units of the same or structurally similar chemical compound of more than one and less than about 30 or 30, and a polymer comprises a higher number of units of the same or structurally similar chemical compounds. A photoinitiator is able to be activated by exposure to light to form a radical. The first functional group is able to be activated by the first photoinitiator, and more specifically, by the radical formed from the first photoinitiator, so that the first component is able to be photo-polymerized through the first functional groups. The first layer is obtained by curing the first mixture, and more specifically, by exposing the first mixture to light such as UV light and/or visible and/or infrared light, and more preferably, light with a wavelength in the range of 200-400 nm.

The second layer is based on a second mixture and/or the second layer is obtained by photo-polymerization (and/or curing) of a second mixture. The second mixture comprises a second photoinitiator and a second component comprising a second monomer or a second oligomer or a second polymer, wherein the second monomer or the second oligomer or the second polymer is an acid and comprises a second functional group. The second photoinitiator is able to be activated by exposure to light to form a radical. The second functional group is able to be activated by the second photoinitiator, and more specifically, by the radical formed from the second photoinitiator, so that the second component is able to be photo-polymerized in a linear way (and/or are to be joined together so as to form a linear polymer chain) through the second functional groups. The second mixture further comprises a base, wherein the base is able to neutralize the second monomer or the second oligomer or the second polymer thereby forming a salt, and a third component comprising at least one of a third oligomer or a third polymer, wherein the third oligomer or the third polymer comprises two or more than two functional groups, said two functional groups being a third functional group and a fourth functional group. Each of the third functional group and the fourth functional group is able to be activated by the second photoinitiator, and more specifically, by the radical formed from the second photoinitiator, so that the third component is able to cross-link the second component through the third and fourth functional groups. The second layer is obtained by curing the second mixture, and more specifically, by exposing the second mixture to light such as UV light and/or visible light and/or infrared light, and more preferably, light with a wavelength in the range of 200-400 nm, so as to form a swelling or superabsorber layer. A swelling capacity of the first layer is smaller than a swelling capacity of the second layer, so that the substrate may be able to curve and/or bend and/or fold itself when contacting liquid including water molecules (and/or dipping and/or submerging in liquid including water molecules). More particularly, the substrate may be able to curve itself when the second layer contacts liquid and is swelled by the liquid, more specifically, is swelled by absorbing a component of the liquid, the liquid including water molecules. When contacting the liquid, the substrate may be able to curve such that a side of the first layer is concave (and/or an inner surface of the substrate) and a side of the second layer is convex (and/or an outer surface of the substrate). Upon contacting the liquid and/or being dipped and/or submerged in the liquid, the substrate preferably curves and/or bends and/or folds itself, such that a radius of curvature of the folded or curved substrate is defined in the z-direction and/or the direction being from the second layer to the first layer and/or the direction from the first surface to the second surface of the first layer, the second surface being opposite to the first surface in the z-direction. The first layer (and/or the first mixture) and the second layer (and/or the second mixture) are preferably electrical insulating material(s). The first layer has preferably a thickness in the z-direction 5 to 200 μm, more preferably 50 to 80 μm, and the second layer has preferably a thickness in the z-direction 5 to 200 μm, more preferably 40 to 80 μm. A radius of curvature of the folded or curved substrate is preferably 50 to 1000 μm, more preferably 50 to 150 μm.

The substrate of the present disclosure may have one or more of following advantages: The photopoymerization process may allow control over the size, shape, and thickness of the first and second layer. The first and second layer may be produced with thicknesses in the micrometer to millimeter range and with lateral dimensions in the micrometer to centimeter range. Moreover, the first and second mixture employed for obtaining the substrate according to the present disclosure may be suitable for modern fabrication techniques such as 3D printing. The second layer is capable of generating a high osmotic force in the polymer network caused by free ions inside the cured polymer network and allows a high swelling of the second layer. Consequently, the second layer functions as a superabsorber layer with a high swelling capacity allowing strong deformations of the substrate. On that account, the second layer, or swelling or superabsorber layer, expands volumetrically when contacting liquid including water molecules, which creates a stress against the first layer or flexible non-swelling base layer. The stress is released by curving or folding of the substrate since the first/second layer undergoes a lower/ larger volumetric change than the second/first layer, respectively. The first layer is flexible and/or elastic in the sense of that it is be capable of being folded and/or curved without breaking. The second layer (superabsorber layer) of the substrate of the present disclosure swells strongly, which allows for small folding radii in the micrometer- or millimeter-range and in general, enables a reliable, stable, and controlled self-curving or self-folding mechanism of the substrate. Since the folding is induced by contact of the substrate and/or second layer to liquid including water molecules (exposure by contact and/or by dipping and/or submerging in the liquid), the substrate provides a stable and reliable mechanism of self-folding or self-assembling that is controllable by an external stimulus. This characteristic may be further advantageous in that, in case the substrate is used for an implantable microelectrode such as a microelectrode or cuff electrode for bioelectronics, the implantable microelectrode can wrap around a biological sample such as a nerve tissue via self-folding during implantation without any further measures that otherwise would have to be carried out manually by the operating personnel. The substrate of the present disclosure may be further advantageous in that the folding or curving is reversible. More precisely, if the substrate (or at least the second layer) in the folded-state is allowed to dry after having contacted liquid including water molecules, the substrate reverts to an unfolded or uncurved state.

The first functional group and/or the second functional group and/or the third functional group and/or fourth functional group can each be an acrylate or methacrylate group. Alternatively, the first, second, third, and fourth functional groups may be an epoxy group, or aromatic ring structure, or chosen from a sulfhydryl (thiol) group or alkene (ene) group for thiol-ene click reaction. Each of the first, second, third and fourth functional groups may comprise covalent bond(s), preferably C=C double bonds, that can be cleaved and photo-polymerize. The radicals for this reaction are generated from the first photoinitiator and the second photoinitiator comprised in the first and second mixture, respectively, which undergo photolysis under irradiation with light such as UV and/or visible light, and/or infrared light, and more preferably, light with a wavelength in the range of 200 to 400 nm. The concentration of the photoinitiator added to the mixture is preferably in the range of 0.1-2% w/w.

The first and second photoinitiator can be the same or different. In particular, the second photoinitiator may be chosen from a group including photoinitiators that are miscible in the second mixture comprising an acid. Examples of the first and/or second photoinitiator would be B(2,4,6-trimethylbenzoyl)phenylphosphine oxide/ethyl(2,4, 6-trimethylbenzoyl)phenylphosphinate (Omnirad 2100) or phenyl bis(2,4,6-trimethylbenzoyl)-phosphinoxide (Omnirad 819 DW).

The second monomer or second oligomer or second polymer of the second mixture may be chosen from a group including acrylic acid, methacrylic acid, ethylene acrylic acid, and polyacrylic acids.

The third component may comprise a third oligomer and/or third polymer that preferably has two or more functional groups, and the functional groups may be acrylate and/or methacrylate functional groups. More preferably, the third oligomer/third polymer is a di-functional oligomer/ polymer that has two acrylate groups or two methacrylate groups. The third oligomer or third polymer preferably is a hydrophilic oligomer or polymer that is miscible in aqueous solutions and may be chosen from a group including methylenebisacrylamide, diethylene glycol diacrylate, triethylene glycol diacrylate, tetraethylene glycol diacrylate, and generally polyethylene glycol diacrylates or dimethacrylates with a number of ethylene glycol blocks of 2 or more.

The substrate is preferably biocompatible, i. e. the material of the first and the second layer of the substrate do not invoke significant cytotoxic effects or show a metabolic inhibition of less than 30% in a WST-8 based cytotoxicity test. A sub-layer and/or adhesive layer may be stacked between the first and the second layer.

Preferably, at least one of the second, third and fourth functional groups is able to form a covalent bond with the first functional group. Unreacted functional groups may still be present in a cured polymer network after a certain curing level (and/or applied curing dose). This feature may be further advantageous in that the first and second layer can be tightly bonded together via covalent bonding even without the use of an adhesive layer.

Preferably, a ratio of the swelling capacity ($Q_{w2}$) of the second layer to the swelling capacity ($Q_{w1}$) of the first layer is preferably $Q_{w2}/Q_{w1}=5$ or more (i.e. $Q_{w1}:Q_{w2}=1:5$ or more), more preferably $Q_{w2}/Q_{w1}=10$ or more (i.e. $Q_{w1}:Q_{w2}=1:10$ or more), more preferably $Q_{w2}/Q_{w1}=20$ or more (i.e. $Q_{w1}:Q_{w2}=1:20$ or more). The ratio is preferably in a range of $Q_{w2}/Q_{w1}=5$ to 20, more preferably in a range of $Q_{w2}/Q_{w1}=10$ to 20. The swelling capacity of the first (second) layer is obtained by dividing (i) a mass of the first (second) layer after the first (second) layer has been contacted liquid including water molecules and/or swelled and/or saturated by components of the liquid, by (ii) an initial mass of the first (second) layer (i.e. a mass of the first (second) layer before contacting the liquid). The second layer is a superabsorber layer with a high swelling capacity, which allows a strong deformation of the substrate and generally enables a reliable, stable, and controlled self-curving and self-folding mechanism of the substrate.

Preferably, the second layer entirely covers the first surface of the first layer. Each of the first layer and the second layer has a length in the x-direction and a width in the y-direction. Preferably, the length of the second layer is shorter than the width of the second layer, wherein the length of the second layer is shorter than the length of the first layer. Preferably, the second layer extends at least 60%, more preferably at least 80%, of the entire extent of the first layer in the y-direction, and more preferably, the width of the first layer may be equal to the width of the second layer.

Preferably, the substrate comprises a plurality of the second layers deposited on the first surface of the first layer, wherein the plurality of the second layers is separated from each other in the x-direction. Preferably, the length of the first layer is longer than the width of the first layer, or the length of the first layer is shorter than the width of the first layer. The first surface of the first layer may be rectangular or rhombic. Preferably, the first layer comprises a groove or dent or recessed portion formed on the first surface of the first layer and/or the second surface of the first layer, the second surface being opposite to the first surface in the z-direction, wherein the groove extends in the x-direction and preferably, the groove extends at least 60%, or more preferably at least 80% of the entire extent of the first layer in the x-direction or more preferably, the entire extent of the first layer in the x-direction. Preferably, the first layer has a third surface in the yz-plane and fourth surface in the yz-plane opposite to the third surface in the x-direction, and the groove extends along the x-direction entirely from the third surface of the first layer to the fourth surface of the first layer. The groove preferably extends through the first layer in the x-direction. The thickness of the first layer in the z-direction at the dent portion is smaller than the other part of the first layer, and the width of the groove is in the y-direction and is shorter than the length of the groove in the x-direction. Consequently, the groove has a longer direction extending in the x-direction.

The substrate according to the present disclosure may have one or more further following advantageous: A direction of curving or folding of the substrate can be more accurately controlled by the plurality of the second layers, such that the substrate curves or folds along the longer side of the second layers. More precisely, if the longer side and/or a main longitudinal direction of the second layers extends in parallel to the y-direction, the substrate curves or folds itself, when contacting liquid including water molecules (and/or being dipped and/or submerged in the liquid), such that the axis of curvature and/or curving and/or folding is defined in the x-direction or in parallel to the x-direction, and the curving radius is defined in the yz-plane.

Preferably, the first layer comprises a plurality of the grooves, wherein the plurality of the grooves is separated from each other in the y-direction. Preferably, the second layer at least partly penetrates into the groove, and more preferably fills up the groove. The second layer may fill up the groove at the position where the groove and the second layer overlay or intersect each other, which may promote the adhesion between the stacked layers. Preferably, the direction of the width of the second layer (and/or the longer direction of the second layer and/or the main longitudinal direction of the second layer) and the direction of the length of the groove (and/or the longer direction of the groove or the direction into which the groove extends) are orthogonal to each other.

The substrate of the present disclosure may further have one or more of the following advantages: The curving direction or folding direction of the substrate along the length of the second layer and/or the longer direction of the second layer and/or the main longitudinal direction of the second layer is promoted by the groove(s) and more pronounced, and it is further possible to precisely control the curving direction and to achieve a smaller curving radius.

Preferably, the first monomer or the first oligomer or the first polymer is a polyurethane or silicone, and the first functional group is an acrylate or methacrylate group. Preferably, the second component comprises the second monomer and the second monomer is acrylic acid or methacrylic acid, and the second functional group is an acrylate or methacrylate group.

Preferably, the second component comprises a further monomer or a further oligomer, which comprises a fifth functional group, wherein the second and the fifth functional group are able to be activated by the second photoinitiator, so that the second component is able to be photo-polymerized in a linear way through the second and fifth functional groups. The substrate according to the present disclosure may be further advantageous in that the swelling properties of the cured polymer network of the second layer can be further controlled by co-polymerizing the second monomer, second oligomer, or second polymer with the further monomer or further oligomer. The further monomer or further oligomer may be a hydrophilic acrylic monomer or oligomer such and may be selected from a group including (meth) acrylated carboxylic acids, amides, and alcohols.

Preferably, the fifth functional group is a methacrylate group, and the further monomer is hydroxyethylmethylacrylate (HEMA). The substrate according to the present disclosure may have one or more of the following advantages: The methyl group in the methacrylate group can cause steric hindrance, and the reactivity of the further monomer with respect to the photo-polymerization would be reduced in comparison to a further monomer comprising an acrylate group as fifth functional group or in comparison to a second monomer, second oligomer, or second polymer comprising an acrylate group as a second functional group. The reaction speed of the photo-polymerization of the second mixture can be more precisely controlled which is specifically important for the processability of the second mixture with modern 3D printing techniques where precise control over layer curing, polymerization depth, and gelation of the material is required.

Preferably, the base comprises NaOH and/or KOH, and the third oligomer or the third polymer is a polyethylene glycol, and the third functional group is an acrylate or methacrylate group, and the fourth functional group is an acrylate or methacrylate group.

Preferably, the molar ratio of the second monomer or the second oligomer or the second polymer to the further monomer or the further oligomer is in a range of 1000:1 to 1:1, or more preferably 1000:1 to 2:1, and/or the molar ratio of the second monomer or the second oligomer or the second polymer to the base is in a range of 10:1 to 10:6. More preferably, the molar ratio of the second monomer or the second oligomer or the second polymer to the base is in a range 10:3 to 10:4.

Preferably, the neutralization degree of the acid to the base is 10 to 60%, or more preferably 30 to 40%. The neutralization degree of a neutralization reaction between the acidic second monomer or second oligomer or second polymer and the base is the ratio between the number of neutralized second monomer or second oligomer or second polymer molecules after the neutralization reaction with the base vs. the initial number of acidic second monomer or second oligomer or second polymer molecules. The neutralization degree is the molar ratio between the initially present acidic second monomer or second oligomer or second polymer molecules and the base.

Preferably, the molar ratio of the second component to the third component is in a range of 1000:1 to 2:1, or more preferably 200:1 to 20:1.

Preferably, the first mixture and/or the second mixture further comprises a further photoinitiator, and/or quencher, and/or a photoabsorber. Examples for an absorber or photosensitizers are 4-hydroxy benzophenone (HMBS) or 2-Isopropylthioxanthone (ITX). An example for a quencher or free-radical quencher is 2,2,6,6-tetramethylpiperidine-1-oxyl (TEMPO). The concentration of the absorbers comprised in the mixtures is preferably in a range of 0% to 10% w/w. The concentration of a quencher comprised in the mixtures is preferably in a range of 0% to 2% w/w.

Preferably, a system according to the present disclosure comprises the above-described substrate and a third layer extending from the first layer in the x-direction and in the y-direction and/or in the xy-plane. The third layer is integrally formed with the first layer and the third layer is preferably based on the first mixture.

Preferably, an electrode element for being implantable into a biological sample comprises the above-described substrate and a first electrical conductive layer deposited on a second surface of the first layer. The second surface extends in the x-direction and in the y-direction and being opposite to the first surface in the z-direction. Therein, the second layer, the first layer, and the first electrical conductive layer are stacked in the z-direction in this order. The second layer, the first layer and the first electrical conductive layer overlap each other in the z-direction.

The electrode element of the present disclosure may have one or more of following advantages: Since the folding of the substrate of the electrode element is induced by contact of the electrode element and/or the substrate of the electrode element and/or the second layer of the substrate to liquid including water molecules and/or by dipping and/or sub-merging the electrode element in the liquid, the electrode element provides a reliable and stable mechanism for self-folding or self-assembling that is controllable by the external stimulus. This characteristic may be further advantageous in that, in case the electrode element is used for implantation into a biological sample, the electrode element can wrap around a biological tissue such as a nerve tissue via self-folding during implantation in a controlled and reliably way. Furthermore, the second layer of the substrate of the electrode element provides a stronger volumetric expansion than the first layer of the substrate, which may allow the electrode element to reliably and stably provide a small folding or curving radius in the micrometer or millimeter range. This may produce a stable and close interface to the biological tissue or nerve, which may enable an improved signal recording and stimulation efficiency.

Preferably, the first electrical conductive layer comprises a metal film and/or a nanoparticle conductor and/or a conductive polymer. The electrical conductive layer may be deposited via sputtering (for example gold or platinum) and/or solution-processing and/or vapor deposition, via solution-processing techniques, and/or by printing and sintering of metal nanoparticle based pastes or inks, and/or by printing of conductive-polymer based pastes or inks. The above-described electrode element may comprise one or more of the optional features of the substrate.

Preferably, an electrode system comprises the above-described electrode element and a third layer extending from the first layer of the substrate of the electrode element in the x-direction and in the y-direction and/or in the xy-plane. The third layer is integrally formed with the first layer. The third layer is preferably based on the first mixture, i.e. the third layer is obtained by curing the first mixture via exposure to light. The electrode system further comprises a second electrical conductive layer deposited on the third layer, wherein the second electrical conductive layer is connected to the first electrical conductive layer, and more particularly, the second electrical conductive layer is mechanically or physically connected to the first electrical conductive layer.

The electrode system of the present disclosure may have one or more of following advantages: Since the folding of the substrate of the electrode element of the electrode system is induced by contact of the electrode system and/or the electrode element of the electrode system and/or the sub-strate of the electrode element and/or the second layer of the substrate to liquid including water molecules and/or by dipping and/or submerging the electrode system and/or the electrode element in the liquid, the electrode system provides a controlled, reliable, and stable mechanism for self-folding or self-assembling. This characteristic may be further advantageous in that, in case the electrode system implanted into a biological sample, the electrode element of the electrode system can wrap around a biological tissue such as a nerve via self-folding during the implantation procedure in a controlled and reliably way. Furthermore, the second layer of the substrate of the electrode system undergoes a stronger volumetric expansion in comparison to the first layer of the substrate, which may allow the electrode element of the electrode system to reliably and stably interface the biological tissue. The electrode element of the electrode system may provide a stable and close interface to the biological tissue or nerve, which may improve the signal recording and stimulation efficiency provided by the electrode system when the second electrical conductive layer of the electrode system is connected to external amplification and/or stimulation circuitry and/or a pulse generator.

The third layer may have a larger thickness than the first layer. The electrode system according to the present disclosure may be further advantageous in that connectors can be more easily attached to the second electrical conductive layer, which improves the reliability of the electrode system.

Preferably, the electrode system further comprises a fourth layer or passivation layer deposited on a third surface of the second electrical conductive layer. The fourth layer is preferably electrical insulating material(s). The third layer, the second conductive layer, and the fourth layer are stacked in the z-direction in this order. The fourth layer is preferably based on the first mixture, i.e. the fourth layer is obtained by curing the first mixture with exposure to light. The above-described electrode system may comprise one of more of the optional features of the electrode element and the substrate.

According to the present disclosure, a method for manufacturing a substrate as described above is provided. The method comprises a step of forming the first layer by exposing the first mixture to light and a step of forming the second layer on the first layer by exposing the second mixture to light. The step of forming the first layer and the step of forming the second layer on the first layer may be performed by using mask-based photolithography techniques, or by using 3D printing such as stereolithography.

Preferably, the step of forming the first layer includes forming the groove. The step of forming the first layer may include a first step of obtaining the first layer by exposing the first mixture to light and at the same time, forming the groove by exposing the first mixture with a light pattern or mask such that the first mixture receives a lower light dose at the local position of the groove compared to the rest of the first mixture. Next, uncured residues of the first mixture may be removed.

According to the present disclosure, the method for manufacturing an electrode element as described above comprises all the steps of the above-described method for manufacturing the substrate and further preferably comprise a step of forming the first electrical conductive layer on the first layer.

A method for manufacturing an electrode system as described above comprises all the steps of the above-described method for manufacturing the electrode element, and further comprises a step of forming the third layer by exposing the first mixture to light, and a step of forming the second electrical conductive layer. The third layer and the first layer can be formed simultaneously by exposing the first mixture with a light pattern or mask, or more preferably, with a grey-scaled pixelated mask generated by a digital micromirror device and/or a stereolithographic printer.

BRIEF DESCRIPTION OF THE DRAWING

In the following detailed description, preferred embodiments of the present disclosure are described with reference to the enclosed drawing in which FIG. 1a schematically illustrates a substrate according to a first embodiment of the present disclosure in a perspective view;

FIG. 1b schematically illustrates a substrate according to a second embodiment of the present disclosure in a perspective view;

FIG. 2a schematically illustrates the substrate according to the first embodiment in a top view;

FIG. 2b schematically illustrates the substrate according to the second embodiment in atop view;

FIG. 3a schematically illustrates a folded or curved substrate according to the first embodiment in a perspective view;

FIG. 3b schematically illustrates a folded or curved substrate according to the second embodiment in a perspective view;

FIG. 8a schematically illustrates the substrate with the first layer having the groove at a first surface according to the third embodiment in a side view;

FIG. 8b schematically illustrates a substrate with a first layer having a groove at a second surface according to the third embodiment in a side view;

FIG. 9a schematically illustrates a folded or curved substrate with the first layer having the groove at the first surface according to the third embodiment in a side view;

FIG. 9b schematically illustrates a folded or curved substrate with the first layer having the groove at the second surface according to the third embodiment in a side view;

FIG. 10a shows a picture of folded or curved substrates according to the second embodiment;

FIG. 10b shows an example of a folded or curved system according to an embodiment of the present disclosure;

FIG. 10c shows an example of a folded or curved system according to an embodiment of the present disclosure;

FIG. 11a schematically illustrates an electrode element according to an embodiment in a side view;

FIG. 11b schematically illustrates a folded or curved electrode element according to an embodiment in a side view;

DETAILED DESCRIPTION OF EMBODIMENTS

1. Substrate

First Embodiment

Figure 4:
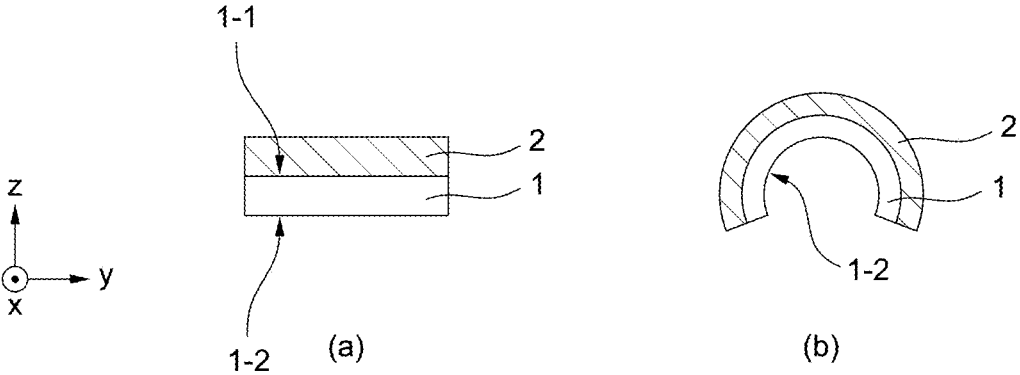
FIG. 4a schematically illustrates the substrate according to the first or second embodiment in a side view.
FIG. 4b schematically illustrates a folded or curved substrate according to the first or second embodiment of the present disclosure in a side view.

FIG. 1*a* (perspective view) and FIG. 2*a* (top view, xy-plane) show a substrate A according to the first embodiment. The substrate A comprises a first layer 1 and a second layer 2. The first layer 1 is a polymer-based flexible layer, which would serve as a base layer, onto which a further structure, for example, an electrode, may be formed. The first layer 1 may include a non-swelling polyurethane or hydrophobic molecules, for example silicone. The second layer 2 is a swelling or superabsorber layer, which would induce the self-curving process of the substrate A. The first and second layers 1, 2 are based on a first mixture 10 and a second mixture 20, respectively. More specifically, the first (second) layer 1 (2) is obtained by photo-polymerization (and/or curing) of a first (second) mixture 10 (20).

Each of the first layer 1 and the second layer 2 extends in the x-direction and in the y-direction. The first layer 1 and the second layer 2 overlap each other in the z-direction. More specifically, as presented FIG. 1*a* and FIG. 2*a*, the second layer 2 may entirely cover a first surface 1-1 of the first layer 1. The first layer 1 has a length $l_1$ in the x-direction and a width $w_1$ in the y-direction. The width $w_1$ of the first layer 1 is preferably shorter than the length $l_1$ of the first layer 1. Correspondingly, the second layer 2 has a length $l_2$ in the x-direction and a width $w_2$ in the y-direction, wherein the width $w_2$ of the second layer 2 is preferably shorter than the length $l_2$ of the second layer, which would be further advantageous in controlling the curving direction of the substrate A as will be explained below. The length $l_1$ of the first layer 1 is equal to the length $l_2$ of the second layer, the width $w_1$ of the first layer 1 is equal to the width $w_2$ of the second layer 2.

FIG. 3*a* shows the substrate A as shown in FIG. 1*a* and FIG. 2*a* that is in the folded- or curved-state. As presented in FIG. 3*a*, since a swelling capacity $Q_{w1}$ of the first layer 1 is smaller than a swelling capacity $Q_{w2}$ of the second layer 2, the substrate A is able to curve itself when contacting liquid including water molecules. The substrate curves such that a side of the first layer 1 is concave and a side of the second layer 2 is convex. More precisely, the substrate A according to the first embodiment curves or folds itself so that the second surface 1-2 of the first layer 1 opposite to the first surface 1-1 is an inner surface of the substrate A.

Self-Folding Mechanism of the Substrate

Referring to FIGS. 1*a*, 2*a*, 3*a*, 15*a* to 15*c*, the working principle of the self-curving (or self-folding) mechanism of the substrate A induced by liquid is explained hereinafter:

The second layer 2 is based on the second mixture 20. The second mixture 20 comprises a base and the second monomer or the second oligomer or the second polymer, which is an acid. The acidic second monomer or the second oligomer or the second polymer is neutralised by the base: The hydrogen atom of the OH group of the acidic second monomer or the second oligomer or the second polymer is released and the ion of the base condensates to the second monomer or the second oligomer or the second polymer to form a second monomer or the second oligomer or the second polymer salt. Consequently, the ion of the base can be released again form second monomer or the second oligomer or the second polymer salt molecules when dissolved in aqueous solutions. Since both the remaining, not neutralised molecules of the acidic second monomer or the second oligomer or the second polymer and the neutralized molecules of the second monomer or the second oligomer or the second polymer comprise a second functional group, they are able to be photo-polymerized together in a linear way through the second functional groups. In this linear polymerisation reaction, a radical generated from the photoinitiator opens a C=C double bond in a second functional group of a second monomer or second oligomer or a second polymer molecule or of a second monomer or a second oligomer or a second polymer salt molecule and binds to one end. Thereby a new radical is generated which binds to another second monomer or second oligomer or second polymer molecule or another second monomer or second oligomer or second polymer salt molecule and continues as a chain reaction so as to form a polymer chain comprising the condensated ions of the base.

Since the second mixture 20 further comprises the third component, the third component comprising at least one of a third oligomer or a third polymer, wherein the third oligomer or the third polymer comprises two or more than two functional groups, said two functional groups being a third functional group and a fourth functional group, the third component is able to cross-link the second component through the third and fourth functional groups so as to form a cross-linked polymer network and obtain the second layer if the second mixture is cured by exposure to light. When this cured polymer network of the second layer is immersed into water, the condensated ions of the base can go into solution but stay within the polymer network of the second layer since the O⁻ ion is bound there. This salt solution inside the cured polymer network of the second layer generates an osmotic force which draws water molecules outside of the polymer network into the polymer network and causes a high level of swelling of the second layer.

Figure 15:
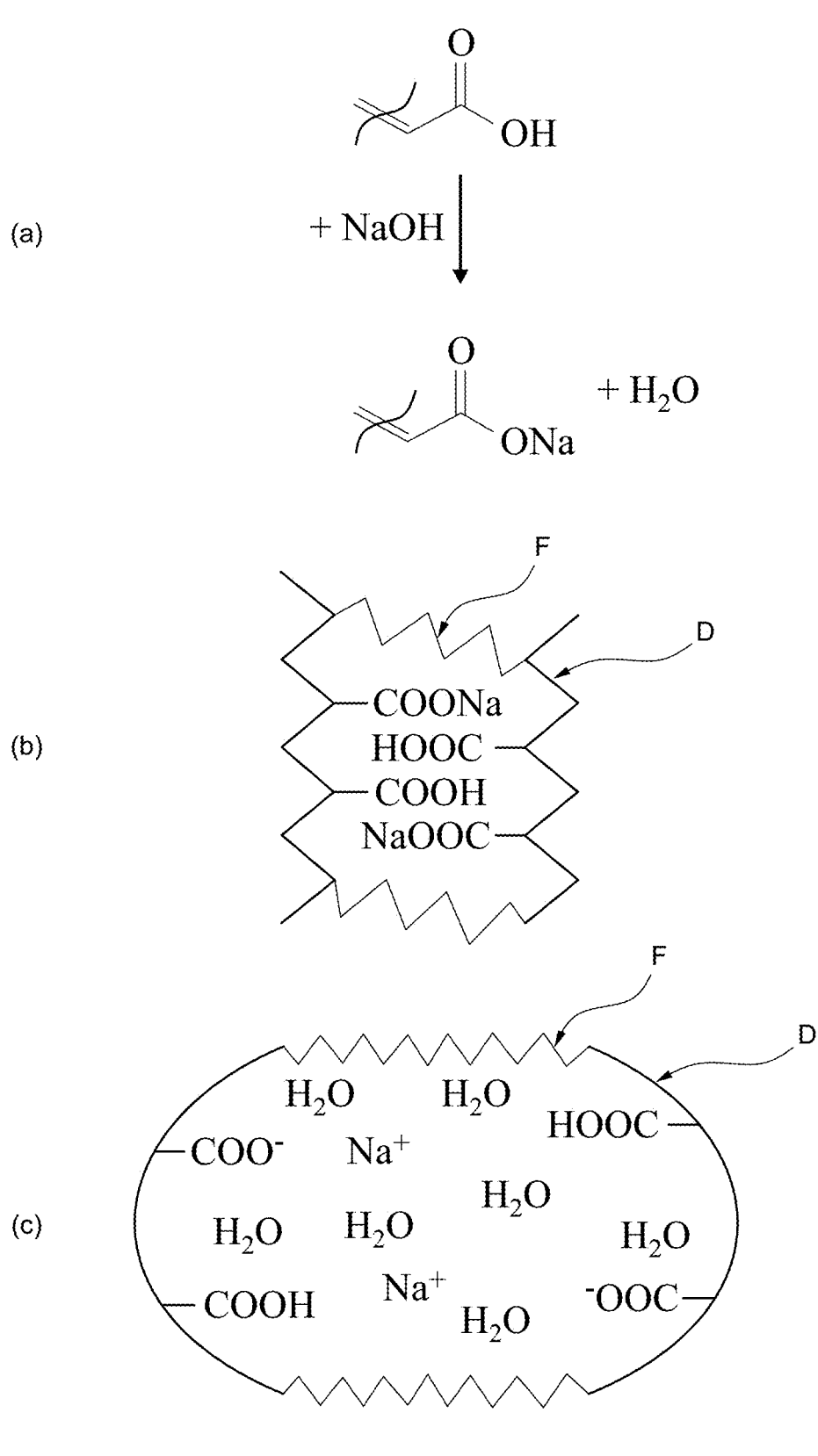
FIG. 15a shows a schematic of the neutralization of the second monomer or a second oligomer or a second polymer with the base according to an embodiment.
FIG. 15*b* shows a schematic of the cured polymer network of the obtained second layer before contacting liquid including water molecules and/or swelling according to an embodiment.
FIG. 15*c* shows a schematic of the cured and swollen polymer network of the obtained second layer that is contacting liquid including water molecules according to an embodiment the present disclosure.

FIGS. 15*a* to 15*c* schematically illustrates the chemical structure of the second layer according to the first embodiment: FIG. 15*a* shows a schematic of the neutralization of the second monomer (here, acrylic acid as an example of the second monomer) of the second mixture 20 with the base (here, NaOH as an example of the base) of the second mixture 20. The neutralization degree or molar ratio of the second monomer to the base is preferably in a range of 10:1 to 10:6. The hydrogen atom of the OH group of the second monomer (acrylic acid) is released and the ion (Na⁺) of the base (NaOH) condensates to the second monomer (acrylic acid) to form a salt of the second monomer (sodium acrylate salt) and a water molecule. The Na⁺ ion of the base can be released again form the salt of the second monomer (sodium acrylate salt) when the second layer 2 is contacting the liquid including water molecules.

FIG. 15*b* shows a schematic of the cured polymer network of an obtained second layer 2 of a substrate A before contacting liquid and/or being swelled by the liquid including water molecules. As presented in FIG. 15*b*, the remaining, not neutralized second monomer (acrylic acid) and the neutralized second monomer (sodium acrylate salt) are able to be photo-polymerized together in a linear way through the second functional groups and form linear polymer chain(s)

D. The third oligomer or the third polymer of the third component in the second mixture 20 cross-links the linearly photo-polymerized second monomer and/or linear polymer chain D to form cross-linker chain(s) F.

FIG. 15*c* shows a schematic of a polymer network of FIG. 15*b* when contacting liquid including water molecules. The $Na^+$ ions of the base can be released form the neutralized and photo-polymerized second monomer and go into solution when the second layer 2 is contacting liquid including water molecules. However, the solvated $Na^+$ ions stay within the polymer network of the second layer 2 since the $O^-$ ions are bound there. This salt solution inside the cured polymer network of the second layer 2 generates an osmotic force which draws water molecules from the outside of the second layer 2 into the polymer network of the second layer 2 and causes a high level of swelling of the second layer 2. As illustrated in FIG. 15*c*, the mesh of the cured polymer network of the second layer 2 comprising cross-linker chain(s) F and linear polymer chain(s) D is stretched and expands volumetrically, which creates a stress against the first layer or flexible non-swelling base layer that comprises a polyurethane. The stress is released by curving or folding of the substrate since the first/second layer undergoes a lower/larger volumetric change than the second/first layer, respectively. The second layer 2 accordingly serves as a superabsorber layer that may allow strong deformations of the substrate A as illustrated in FIG. 3*a*.

The self-curving mechanism and/or approaches disclosed herein generally serve for providing a substrate for an implantable microelectrode, electrode element and electrode system that allow achieving a stable, reliable, and controlled mechanism of self-curving or self-folding. The mechanism is common throughout the following embodiments of the present disclosure.

Second Embodiment

FIG. 1*b*, FIG. 2*b*, and FIG. 4*a* show a substrate A according to an embodiment of the disclosure (the side view of the first embodiment and the second embodiment are identical to each other). The substrate A according to the second embodiment differs from the first embodiment in the configuration/shape of the second layer 2. According to the second embodiment, the second layer 2 covers the first surface 1-1 of the first layer 1 only partly. The width $w_2$ of the second layer 2 may be equal to the width $w_1$ of the first layer 1, or alternatively, the width $w_2$ of the second layer 2 is at least 60% or more preferably at least 80% the width $w_1$ of the first layer 1. The width $w_1$ of the first layer 1 may be equal to the width $w_2$ of the second layer 2. According to the second embodiment, the length $l_2$ of the second layer 2 is shorter than the length $l_1$ of the first layer 1, so that the second layer 2 has a longer side in the y-direction (i.e. the width $w_2$ is longer than the length $l_2$). The substrate A preferably comprises a plurality of the second layers 2 deposited on the first surface 1-1 of the first layer 1, wherein the plurality of the second layers 2 is separated from each other in the x-direction. FIG. 2*b* shows three of the second layer 2 forming stripes on the first surface 1-1 of the first layer 1. The specific number of the second layer 2 shown in FIG. 2*b* is only an example and may be less or more.

FIG. 3*b* and FIG. 4*b* show the substrate A according to the second embodiment that is in the folded- or curved-state, which is after contacting the liquid and having been swelled by the liquid including water molecules. Similar to the first embodiment, since the swelling capacity $Q_{w1}$ of the first layer 1 is smaller than a swelling capacity $Q_{w2}$ of the second layer 2, the substrate A is able to curve itself when contacting liquid including water molecules such that a side of the first layer 1 is concave and a side of the second layer 2 is convex. More specifically, the substrate A curves or folds itself so that the second surface 1-2 of the first layer 1 is an inner surface of the substrate A. The curving or folding direction and/or axis of the substrate A may be more precisely controlled by the shape or geometry of the second layer(s) 2: The substrate A curves or folds along the longer side and/or the main longitudinal direction and/or the width $w_2$ of the second layer(s) 2. More precisely, as presented in FIGS. 1*b*, 2*b*, and 3*b*, the longer side of the second layer(s) 2 and/or the main longitudinal direction of the second layer(s) 2 is along the width $w_2$ of the second layer(s) 2 and/or extends in parallel to the y-direction. Hence, the curving or folding of the substrate A is controlled by the second layer(s) 2 in that the substrate A curves or folds itself along the y-direction. More precisely, as presented in FIG. 3*b* and FIG. 4*b*, the substrate A curves or folds itself such that the axis of curvature is defined in the x-direction and more precisely, is in parallel to the x-direction, and the curving radius is defined in the yz-plane.

Third Embodiment

Figure 5:
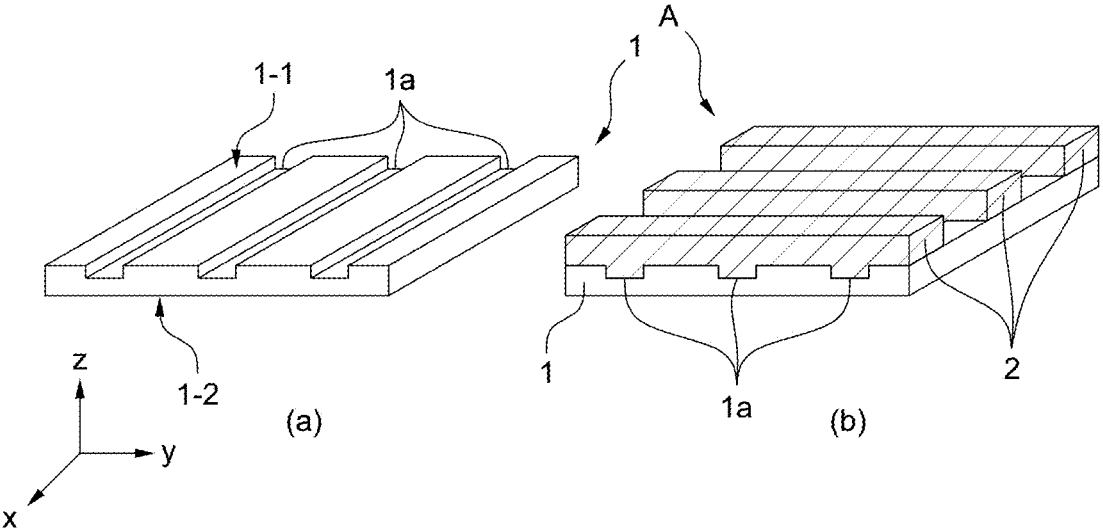
FIG. 5a schematically illustrates a first layer of a substrate having a groove according to a third embodiment in a perspective view.
FIG. 5b schematically illustrates a substrate with the first layer having the groove according to the third embodiment in a perspective view.
Figure 6:
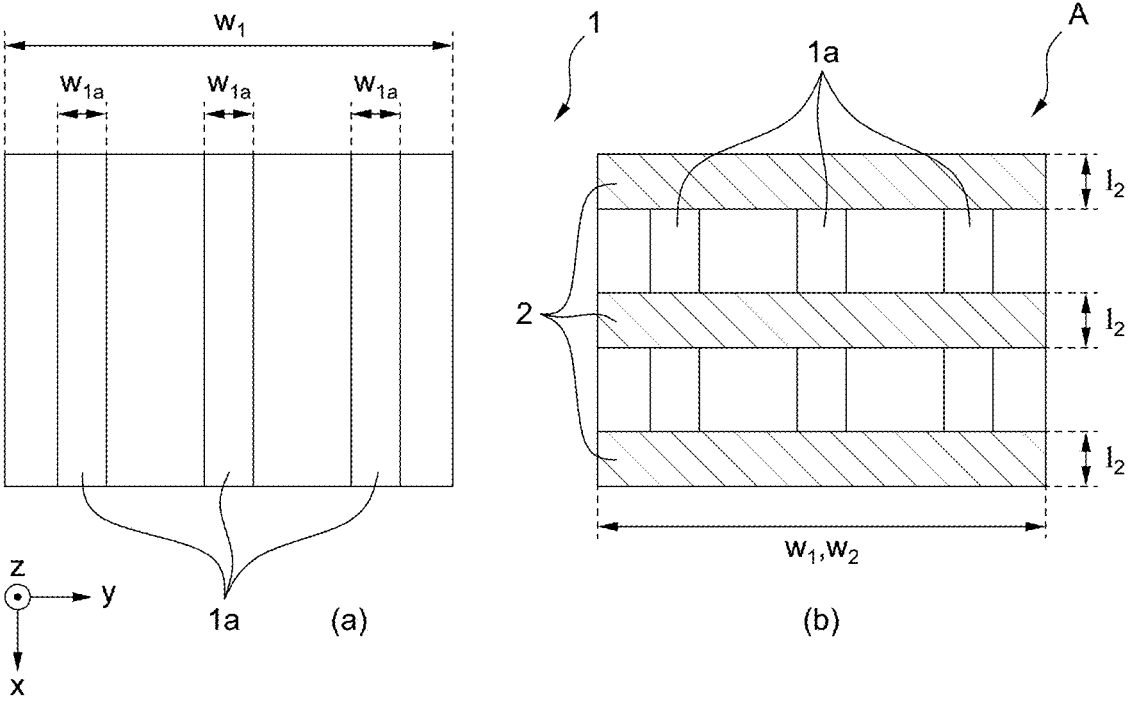
FIG. 6a schematically illustrates the first layer of the substrate having the groove according to the third embodiment in a top view.
FIG. 6b schematically illustrates the substrate with the first layer having the groove according to the third embodiment in a top view.

FIG. 5*a* and FIG. 6*a* show a perspective view and a top view of a first layer 1, respectively, according to the third embodiment. The first layer 1 according to the third embodiment has at least one groove 1*a* or dent or recessed portion at a first surface 1-1 of the first layer 1 for promoting and supporting the self-folding process of the substrate A. The first layer 1 may comprise a plurality of grooves 1*a*. The specific number of the grooves 1*a* shown in FIG. 5*a* and FIG. 6*a* is only an example and may be less or more.

Each of the plurality of grooves 1*a* at the first surface 1-1 of the first layer has a width $w_{1a}$ in the y-direction. The first layer 1 has a width $w_1$ in the y-direction and a length $l_1$ in the x-direction and the width $w_{1a}$ of the groove(s) is smaller than the width $w_1$ of the first layer 1. The grooves 1*a* of the plurality of grooves 1*a* are separated from each other in the y-direction. The groove extends at least 60% of the entire extent of the first layer in the x-direction, and the grooves 1*a* preferably extend through the first layer 1 along the entire length ($l_1$) of the first layer 1 in the x-direction and/or in parallel to the x-direction, as illustrated in FIG. 5*a*. The thickness of the first layer 1 in the z-direction at the grooves 1*a* is smaller than the other part of the first layer 1. FIG. 5*a* and FIG. 6*a* show three of the grooves 1*a* forming stripes on the first surface 1-1 of the first layer 1.

FIG. 5*b* and FIG. 6*b* show a perspective view and a top view of a substrate A, respectively, according to the third embodiment. FIG. 8*a* further shows a side view of the substrate A according to the third embodiment. The substrate A comprises the first layer 1 having the plurality of the grooves 1*a* that promote and support the self-folding process of the substrate, and further comprises a second layer 2. The first layer 1 and the second layer 2 are stacked in the z-direction so that the first layer 1 and the second layer 2 overlap each other. More specifically, the substrate A comprises the second layer 2 that has a longer side and/or main longitudinal direction in the y-direction. In case the width $w_1$ of the first layer 1 is longer than the length $l_1$ of the first layer 1, the second layer 2 may entirely cover the first layer 1, similar to the first embodiment. Preferably, the substrate A comprises a plurality of the second layers 2 and that is separated from each other in the x-direction. The grooves 1*a* in the first layer 1 have a width $w_{ma}$ that is smaller than the width $w_1$ of the first layer 1 and have a longer side and/or main longitudinal direction extending in the x-direction. The direction of the longer side and/or main longitudinal direction of the plurality of the second layer 2 and the longer side and/or the main longitudinal direction of the plurality of grooves 1a are orthogonal to each other. Furthermore, the grooves 1a are open to the top of the first layer 1 towards the plurality of the second layer 2 so that the plurality of the second layer 2 penetrates into the grooves 1a and/or fills up the grooves 1a. As presented in FIG. 5b, the plurality of the second layer 2 fills up the grooves 1a at the positions where the grooves 1a and the plurality of the second layer 2 overlay or intersect each other. FIGS. 5b and 6b show three of the second layers 2 forming stripes on the first surface 1-1 of the first layer 1. The specific number of the second layer 2 shown in FIGS. 5b and 6b is only an example and may be less or more.

Figure 7:
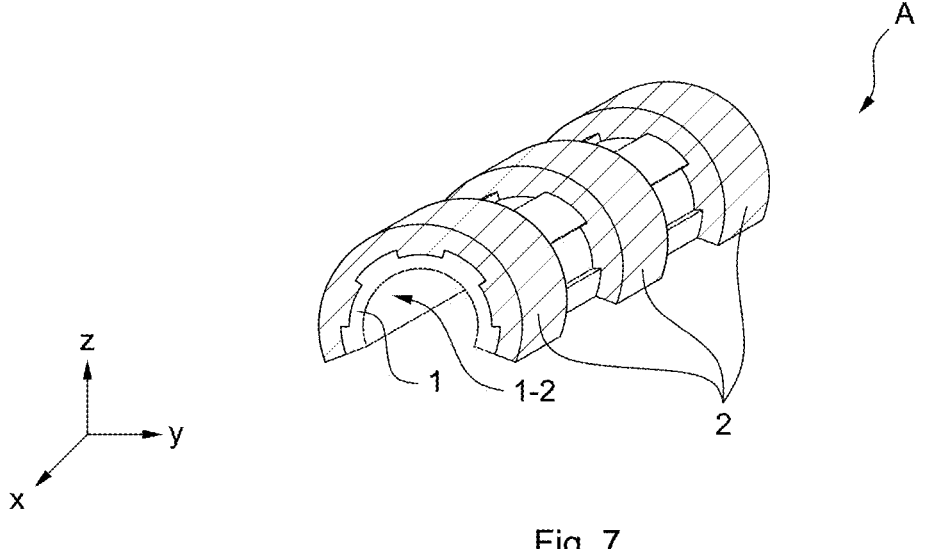
FIG. 7 schematically illustrates a folded or curved substrate with the first layer having the groove according to the third embodiment in a perspective view.

FIG. 7 and FIG. 9a shows a perspective view and a side view of the substrate A, respectively, according to the third embodiment that is folded or curved. The self-curving or self-folding of the substrate A (when contacting liquid including water molecules) is along the longer side or main longitudinal direction of the plurality of the second layer 2 and orthogonal to the longer side and/or main longitudinal direction of the plurality of grooves 1a. The axis of curvature is in the x-direction and/or in parallel to the x-direction. More specifically, the substrate A curves or folds itself so that a side of the first layer 1 is concave (and/or the second surface 1-2 of the first layer 1 is an inner surface of the substrate A) and a side of the second layer 2 is convex.

FIG. 8b shows a side view of a substrate A according to a variation of the third embodiment, in which a first layer 1 has a plurality of grooves 1a at the second surface 1-2. FIG. 9b shows the substrate A of the variation of the third embodiment that is curved or folded. The substrate A curves or bends or folds itself when contacting liquid including water molecules so that a side of the first layer 1 is concave and a side of the second layer 2 is convex. More specifically, the second surface 1-2 having the grooves 1a is an inner surface of the substrate A.

Further Modifications

According to the first to the third embodiment, the second layer 2 may be directly deposited on the first layer 1. Alternatively, the substrate A according to the first to third embodiment may include one or more further sublayers between the first layer 1 and the second layer 2, such as an adhesion layer.

Manufacturing Method

The method comprises a step of forming the first layer 1 by exposing the first mixture 10 to light. More particularly, the first mixture 10 can be placed on a transparent support or glass slide 70 by drop-casting or spin-coating. Then the first mixture 10 is irradiated with a light pattern from below the support 70 to obtain the first layer 1. For the third embodiment (cf. FIG. 5a), the groove(s) 1a would be formed by applying different exposure time and/or light dose to different positions of the first mixture 10: At the position(s) of the groove(s) 1a, a shorter exposure time and/or lower dose is applied than the other part of the first layer 1, so that the first layer 1 at the groove(s) 1a has a thickness in the z-direction smaller than the other part of the first layer 1. The groove(s) 1a are accordingly formed on a surface (extending in x- and y-directions) of the first layer 1.

After exposing the first mixture 10, uncured residues of first mixture 10 are removed. The method further comprises a step of forming the second layer 2 on the first layer 1 by exposing the second mixture 20 to light. Therein, the second mixture 20 is deposited onto the first layer 1 and is exposed to light through the support 70 and the cured first layer 1. The patterning of the second layer 2 (for example, the plurality of stripe-shaped second layers according to the second or third embodiment) may be formed also by exposing a patterning structure, i.e. by exposing only a part of the second mixture 20 to the light, and by subsequently removing uncured residues of the second mixture 20 from the surface of the first layer 1. For the variation of the third embodiment (cf. FIG. 8b), after curing the first layer 1, the first layer 1 is turned around and the second mixture 20 is deposited on a surface without the grooves 1a, and the second layer 2 is further patterned as described above. Alternatively, the grooves 1a on the second surface 1-2 of the first layer 1 can be fabricated by molding from a transparent support or master comprising the positive structures for the grooves 1a.

EXAMPLES

In the following, examples of the substrate A of the present disclosure are described which were manufactured according to the above-described embodiments. The materials and conditions used in the examples are only example and do not restrict the embodiment:

FIG. 10a shows examples of substrates according to the second embodiment, that are in the folded- or curved-state, after contacting and having been swelled by deionized water (the substrate examples are therefore in a saturated state in which the first and/or second layer is/are saturated by components of the liquid). According to the examples, the first layer 1 is based on a first mixture comprising polyurethane 3D printing resin (Luxaprint® flex Detax), which is an example of the first mixture 10 comprising the first component. The second layer 2 is based on a second mixture 20 comprising acrylic acid (molar ratio of 50%), which is an example of a second monomer, HEMA (molar ratio of 25%), which is an example of a further monomer, base NaOH (30% stock in deionized water, molar ratio of 25%), which is an example of a base, PEGDA (Mn 500, molar ratio 1%), which is an example of a third oligomer or cross-linker, Omnirad 2100 (molar ratio 1%), which is an example of a photoinitiator, quencher TEMPO (molar ratio 0.02%), and photoabsorber ITX (molar ratio 0.025%). Both the first layer 1 and the second layer 2 were obtained by curing the first mixture 10 and the second mixture 20, respectively, with exposure to light of a wavelength around 365 nm. The first layer 1 has a length $l_1$ of 3 mm and a width $w_1$ of 1.5 mm, and 8 of the second layers 2. each of which has a length $l_2$ of 0.18 mm and a width $w_2$ of 1.5 mm, were formed on the first layer 1. The first and second layers each have a thicknesses of 0.05 mm. In the folded-state, the substrate examples show a curving radius of 0.5 mm.

FIG. 10b shows four examples (Examples 1, 2, 3, 4 from the most right to the most left of FIG. 10b, respectively) of a system having a substrate A having a form according to the second embodiment. FIG. 10b shows a side view of the examples, i.e. a view in the x-direction and in the yz-plane. Each of the system examples includes an additional layer (third layer) extending from the first layer 1 the substrate A in the x-direction and in the y-direction, which is integrally formed with the first layer 1. The system examples shown in FIG. 10b have the substrate A in the folded-state after contacting the liquid (here deionized water at room temperature) and having been swelled by the liquid including water molecules (the substrates of the system examples are therefore in a saturated state in which the first and/or second layer is/are saturated by components of the liquid). In each of the system examples, the substrate A is disposed at an edge part of the system along the y-direction (i.e. an upper part of the system examples in FIG. 10*b*).

Each of the first layer(s) 1 of Examples 1-4 has a width $w_1$ of 0.6 mm in the y-direction, a length of 0.8 mm in the x-direction and a thickness ($t_1$) of 76 µm in the z-direction. The third layer extending from the substrate A has a thickness of 0.15 mm in the z-direction. Each of the Examples 1-4 has a number of three of the second layer(s) 2. Each of the second layers 2 has a length $l_2$ of 0.15 mm in the x-direction, a width of $w_2$ of 0.6 mm in the y-direction, and the second layers are separated from each other by a distance of 0.15 mm in the x-direction. Examples 1-4 of the system are different from each other in the thicknesses ($t_2$) of the second layer 2, as summarized in Table 1.

FIG. 10*c* shows further four examples (Examples 5, 6, 7, 8 from the most right to the most left of FIG. 10*c*, respectively) of systems that are in the folded- or curved-state. Examples 5-8 have the same configuration as Examples 1-4, except the thickness ($t_1$) of the first layer(s) 1 and the thickness ($t_2$) of the second layers 2. Each first layer 1 has a thickness ($t_1$) of 87 µm in the z-direction. Examples 5-8 are different from each other in the thickness ($t_2$) of the second layer 2 as summarized in Table 2.

According to Examples 1-4 presented in FIG. 10*b* and Examples 5-8 presented FIG. 10*c*, a first mixture 10 comprising polyurethane 3D printing resin (Luxaprint flex Detax) as described above with regard to FIG. 5*a* is prepared. For providing the second mixture 20, second monomer acrylic acid (molar ratio of 50%), further monomer HEMA (molar ratio of 25%), base NaOH (30% stock in deionized water, molar ratio of 25%), third oligomer or cross-linker PEGDA (Mn 500, molar ratio 1%), photoinitiator Omnirad 2100 (molar ratio 1%), quencher TEMPO (molar ratio 0.02%), and photoabsorber ITX (molar ratio 0.025%) are mixed. For a good swelling capacity $Q_{w2}$ of the second layer 2, the neutralization degree or molar ratio of the second monomer to the base is preferably in a range of 10:1 and 10:6. Furthermore, for a stable polymer network structure, the molar ratio of the second monomer to the third oligomer is preferably 1000:0.1 to 2:1.

A stereolithographic printer (Miicraft 50X, LED with wavelength of 365 nm) is used to process the first mixture 10 and second mixture 20 for producing Examples 1-8. A small amount (1-2 ml) of the first mixture 10 is provided and/or drop-casted and/or pipetted onto a support 70 (glass slide) provided in the empty tank of the printer. The first mixture is exposed with a light pattern by use of the printer so as to simultaneously form the first layer 1 and the third layer 4. For Examples 1-4, the first mixture 10 is cured at the position of the first layer 1 with an exposure time of 1 second and/or irradiance of 1 mW cm$^{-2}$ to obtain a thickness $t_1$ of 76 µm, and at the position of the third layer 4 with an exposure time of 10 second and/or irradiance of 1 mW cm$^{-2}$ to obtain a thickness of 150 µm. For Examples 5-8, the first mixture 10 is cured with an exposure time of 2 seconds and/or irradiance of 2 mW cm$^{-2}$ at the position of the first layer 1 with a thickness $t_1$ of 87 µm. Uncured residues of the first mixture 10 are removed by washing with isopropanol. Next, a small amount (50-500 µl) of the second mixture 20 is provided on the first surface 1-1 of the first layer 1. The second layer(s) 2 of Examples 1-4 and Examples 5-8 are obtained by curing the second mixture 20 provided on the first surface 1-2 with different exposure times in the range of 30 to 50 seconds and/or light irradiance of 3 to 5 mW cm$^2$. After curing, residues of the second mixture are removed by washing with isopropanol. The thicknesses of the first layer(s) 1 and the second layer(s) 2 of the Examples were measured using a confocal laser scanning microscope (Keyence VK-X250).

The produced Examples are placed onto a holder and submerged in deionized water for at least 10 min. According to Examples 1-4 presented in FIG. 10*b* and Examples 5-8 presented FIG. 10*c*, the substrates(s) A of the example system(s) curve itself such that the second surface 1-2 of the first layer (1) forms an inner layer of the curved or folded substrate A. The curved or folded Examples 1-8 are investigated using an optical microscope for measuring the curving radius. The results of the measured thicknesses of the first layer(s) 1, thicknesses of the second layer(s) 2, and achieved curving radii of Examples 1-4 are presented in Table 1. The results of the measured thicknesses of the first layer(s) 1, thicknesses of the second layer(s) 2, and achieved curving radii of Examples 5-8 are presented in Table 2.

The results according to Table 1 and Table 2 show that the substrate(s) A according to the present disclosure provide a stable, reliable, and controlled mechanism of self-curving or self-folding. For both thicknesses $t_1$ of the first layer 1, a smaller curving radius was obtained for a larger thickness $t_2$ of the second layer 2. The Examples 1-8 demonstrate that small curving radii in the micrometer range, which is suitable for wrapping/gripping and attaching an electrode to a biological sample such as a nerve fibre having a diameter typically in a range of several tens to several hundred µm, may be reliably and stably achieved by setting the thickness of the second layer(s) 2.

TABLE 1

| ($t_1$ = 76 µm) | | | |
| --- | --- | --- | --- |
| | Example 1 | Example 2 | Example 3 | Example 4 |
| $t_2$ [µm] | 22 | 33 | 45 | 104 |
| Curving radius [µm] | 714 | 141 | 103 | 87 |

TABLE 2

| ($t_1$ = 87 µm) | | | |
| --- | --- | --- | --- |
| | Example 5 | Example 6 | Example 7 | Example 8 |
| $t_2$ [µm] | 32 | 50 | 74 | 113 |
| Curving radius [µm] | 587 | 163 | 128 | 128 |

2. Electrode Element

FIG. 11*a* and FIG. 11*b* show a schematic side view of an electrode element B and a folded or curved electrode element B, respectively. The electrode element B comprises a substrate A according to the first embodiment or the second embodiment or the third embodiment. The electrode element B further comprises a first electrical conductive layer 3 deposited on the second surface 1-2 of the first layer 1 of the substrate A. The first electrical conductive layer 3 may serve as a part of an implantable microelectrode and may directly and/or physically contact a biological sample in a use. The second layer 2 of the substrate A, the first layer 1 of the substrate A, and the first electrical conductive layer 3 are stacked in the z-direction in this order and overlap each other. As presented in FIG. 11*b*, the electrode element B curves itself when contacting liquid including water molecules such that the first electrical conductive layer 3 is an inner layer of the substrate A. The axis of curvature is defined in the x-direction and more precisely, is in parallel to the x-direction and the curving radius is defined in the yz-plane.

For manufacturing the electrode element B, the substrate A according to the first or second or third embodiment is at first prepared according to the manufacturing method of the substrate A. The first electrical conductive layer 3 is deposited on the second surface 1-2 of the first layer 1 of the substrate A by, for example, a metal sputtering process or printing process.

3. Electrode System

Figure 12:
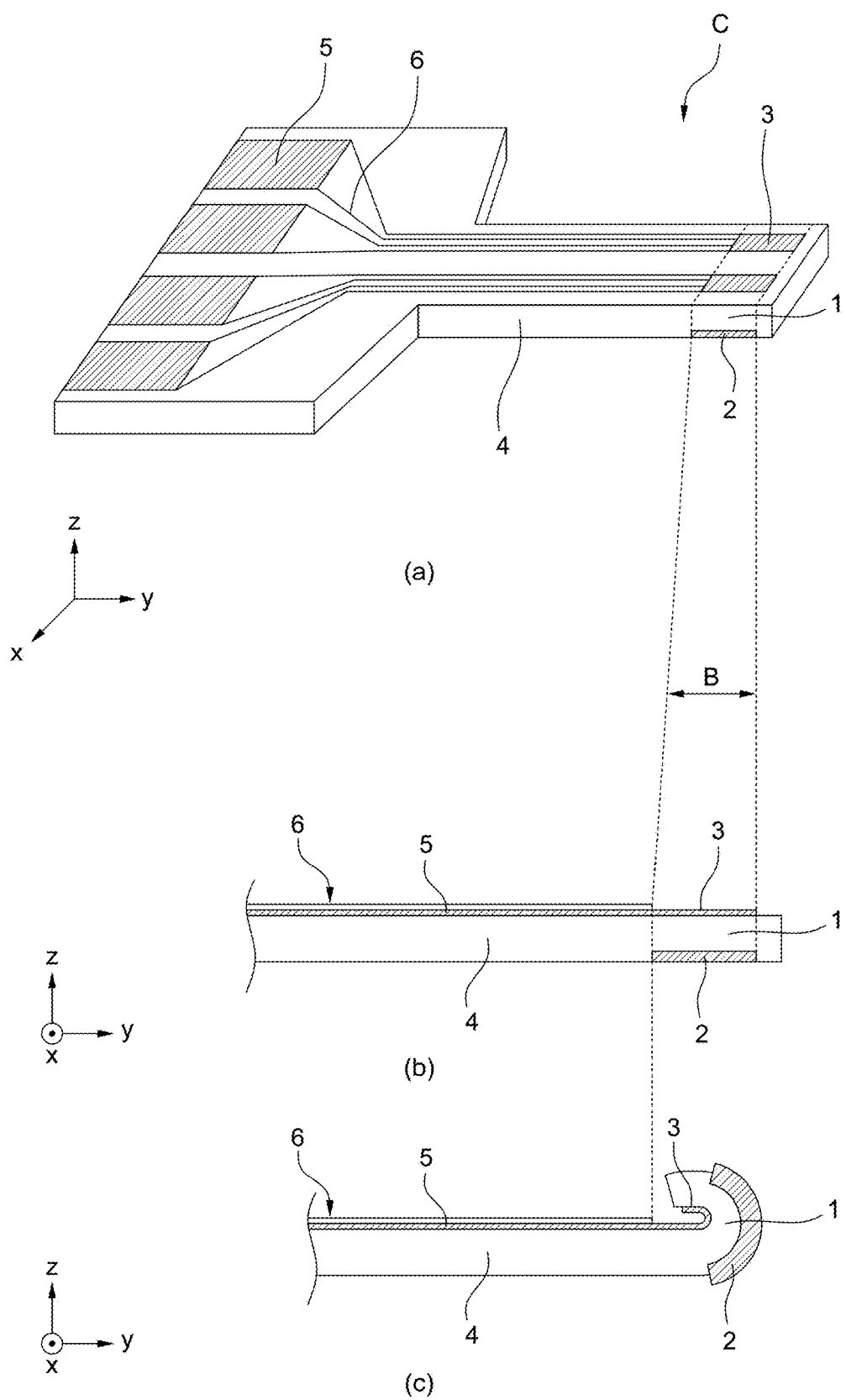
FIG. 12a schematically illustrates an electrode system according to an embodiment in a perspective view.
FIG. 12b schematically illustrates the electrode system according to an embodiment of the present disclosure in a side view.
FIG. 12c schematically illustrates a folded or curved electrode system according to an embodiment in a side view.

FIG. 12a, FIG. 12b, and FIG. 12c schematically show an electrode system C, which comprises the electrode element B. As explained above, the electrode element B includes the first electrical conductive layer 1 being for directly and/or physically contacting a biological sample and includes the substrate A according to the first or second or third embodiment. The electrode system C further includes a third layer 4 extending from the first layer 1 in the x-direction and in the y-direction. The third layer 4 is integrally formed with the first layer 1 of the electrode element B, wherein the third layer 4 is preferably based on the first mixture 10 as well as the first layer 1. The third layer 4 and first layer 1 are obtained by curing the first mixture 10, and more precisely, can be obtained simultaneously by curing the first mixture 10. The electrode system C further comprises a second electrical conductive layer 5 deposited on the third layer 4, wherein the second electrical conductive layer 5 is connected to the first electrical conductive layer 3. More precisely, the second electrical conductive layer 5 is mechanically or physically connected to the first electrical conductive layer 3. The second electrical conductive layer 5 may be formed simultaneously with the first electrical conductive layer 3, for example, in a metal sputtering process. The second electrical conductive layer 5 may serve as a feedline and a contact pad for electrically connecting the first electrical conductive layer 3 to a further instrument. In the embodiment, two feed lines (i.e. the second electrical conductive layer 5) are provided and connected to the one first electrical conductive layer 3, which may be further advantageous in that to perform a conductivity test. The two feed lines are only optional and the first electrical conductive layer may be connected to only a single feed line.

The electrode system C preferably further comprises a fourth layer 6, which may be a passivation layer 6 and/or an insulating layer for shielding a part of the second electrical conductive layer, on a surface of the second electrical conductive layer 5. The third layer 4, the second conductive layer 5, and the fourth layer 6 are stacked in the z-direction in this order. More particularly, the third layer 4, the second conductive layer 5, and the fourth layer 6 overlap each other. The fourth layer 6 may be based on the first mixture 10 and/or the fourth layer 6 is obtained by curing the first mixture 10.

As presented in FIG. 12c, the electrode element B of the electrode system C can curve or fold itself when contacting liquid including water molecules (when at least the second layer 2 of the substrate A contacts the liquid and is swelled by the liquid) such that the axis of curvature is defined in the x-direction and/or is in parallel to the x-direction and the curving radius is defined in the yz-plane. The electrode element B of the electrode system C curves or folds itself so that the first electrical conductive layer 3 forms an inner layer of the curved or folded electrode element B.

Manufacturing Method

Figure 14:
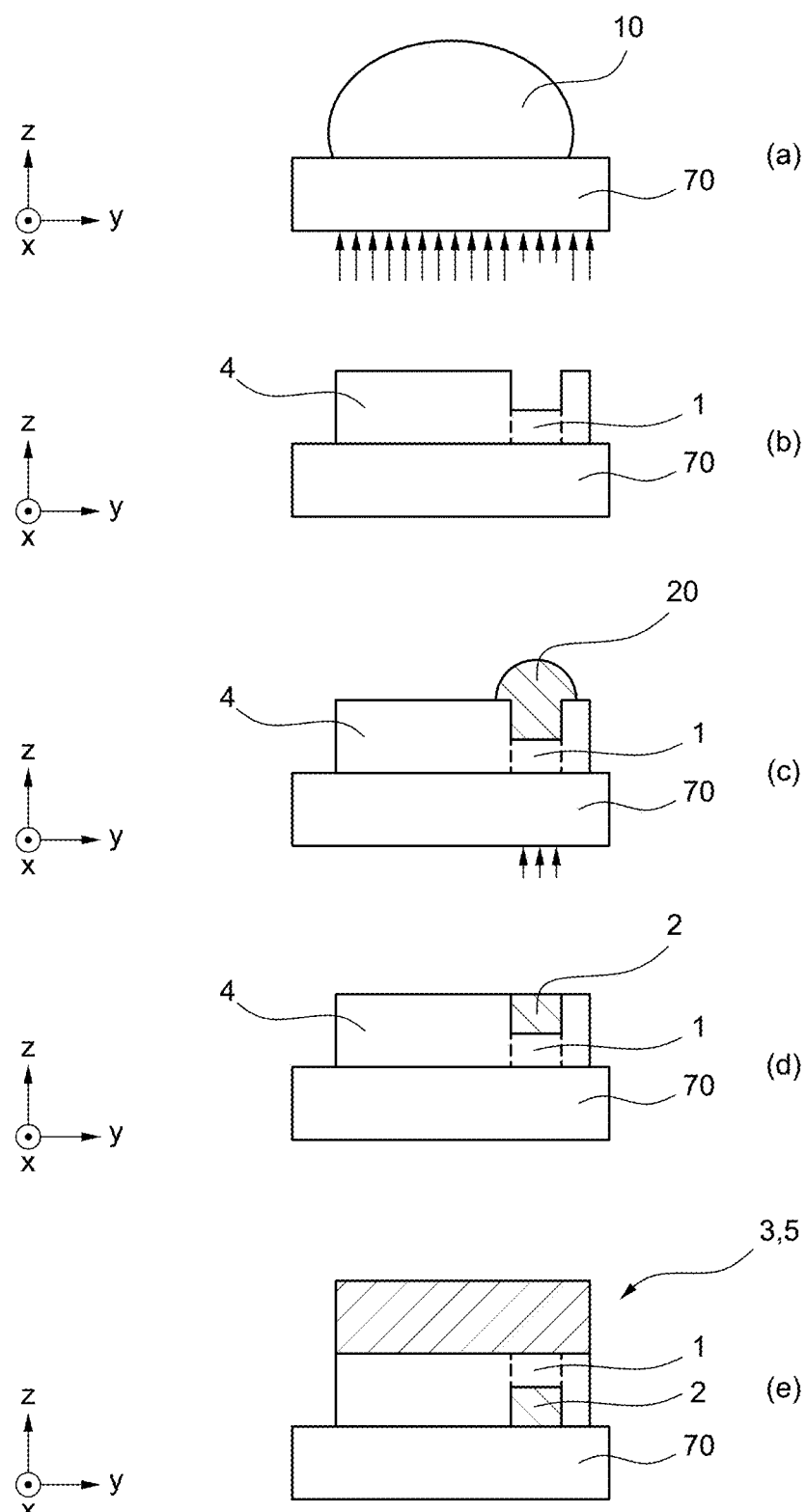
FIGS. 14a-e show a schematic of a method for manufacturing the substrate and/or the electrode system according to the present disclosure.

FIG. 14a-e shows a schematic of a method for manufacturing the electrode system C into which the electrode element B including the substrate A according to the first or second or third embodiment is integrated. As presented in FIG. 14a, the method comprises a step of forming the first layer 1 and the third layer 4 by exposing the first mixture 10 to light. More particularly, the first mixture can be placed on a transparent support or glass slide 70 by drop-casting or spin-coating. Then the first mixture 10 is irradiated with a light pattern (presented as arrows) from below the support 70 to obtain the first layer 1 and the third layer 4. As shown in FIG. 14b, the thickness of the third layer 4 in z-direction is formed to be larger than the thickness of the first layer 1 by applying a longer exposure time and/or higher dose (represented in FIG. 14a by the lengthier arrows) to the first mixture 10 at the position of the third layer 4 in comparison to the position of the first layer 1 (represented in FIG. 14a by the shorter arrows).

After exposing the first mixture 10, uncured residues of first mixture 10 are removed. As shown in FIG. 14c, the method further comprises a step of forming the second layer 2 on the first layer 1 by exposing the second mixture 20 to light. Therein, the second mixture 20 is deposited onto the first layer 1 and is exposed to light through the support 70 and the cured first layer 1 as represented by the arrows. The curing of the first layer 1 with a shorter exposure time than the third layer 4 may be particularly advantageous in that, in case both the first mixture 10 and the second mixture 20 comprise a first and second component with (meth)acrylate functional groups, the first layer 1 and the second layer 2 may covalently bond to each other via the (meth)acrylate functional groups which may yield strong adhesion between the first layer 1 and the second layer 2, even without an adhesion layer between the first and second layers.

As shown in FIG. 14d, uncured residues of the second mixture 20 are removed after curing the second mixture 20 to obtain the second layer 2. As shown in FIG. 14e, the formed first layer 1, second layer 2, and third layer 4 are turned up-side down onto the support 70 and the method further comprises a step of forming the first electrical conductive layer 3 on the first layer 1 and a step of forming the second electrical conductive layer 5 on the third layer 4.

EXAMPLES

In the following, examples are described with respect to an electrode system C according to the present disclosure. The materials and conditions used in the examples are only example and do not restrict the embodiment.

Figure 13:
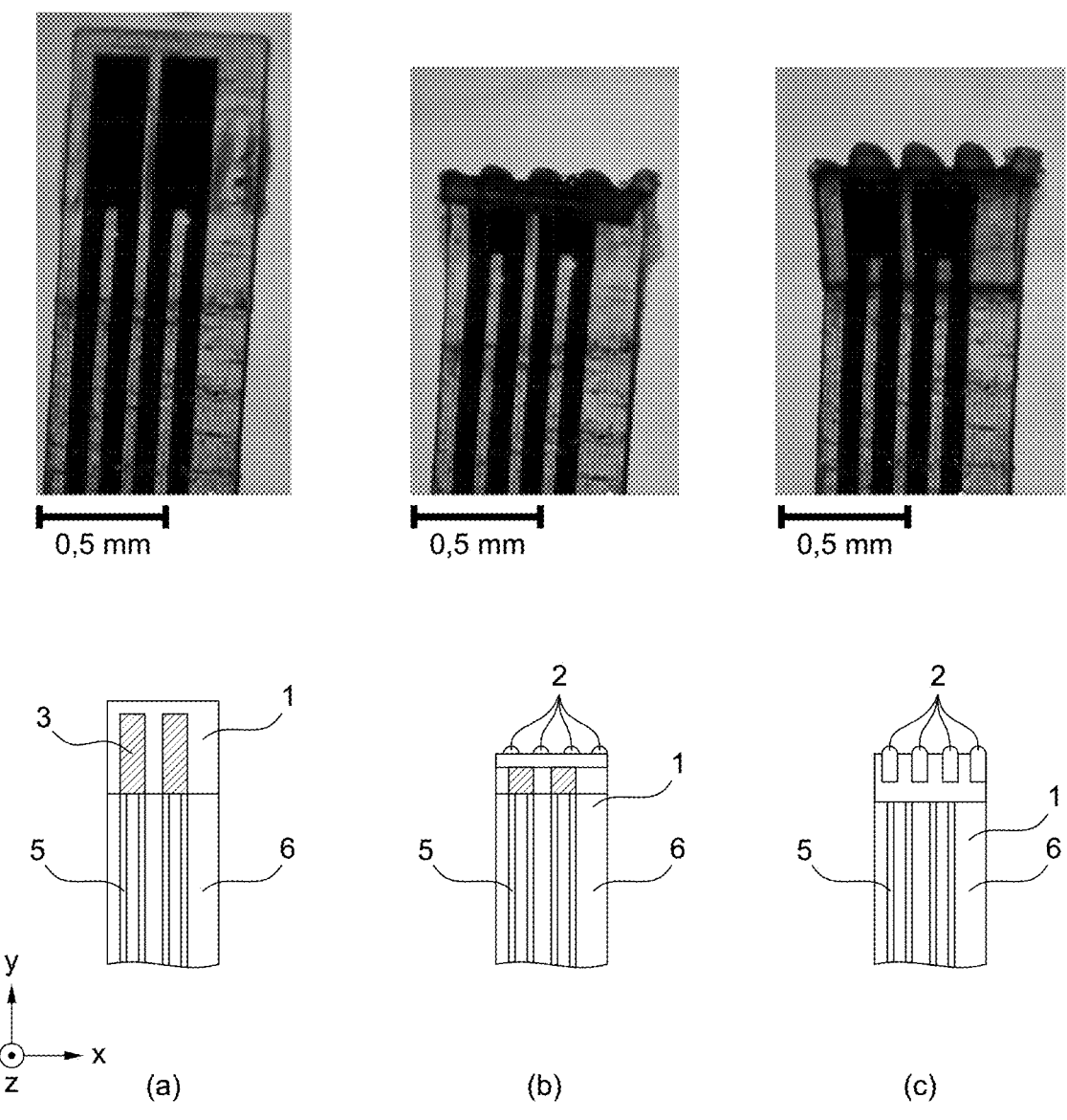
FIGS. 13a-c show an example of a curving electrode system according to an embodiment in a top view.

FIGS. 13a-c show a part of an example of a curving electrode system C according to an embodiment (pictures of the example are shown on the upper row and the corresponding schematic illustrations are shown on the lower row). The first layer 1, the second layer 2, and the third layer 3 of the electrode system C is obtained from the first mixture 10 and second mixture 20, respectively, as described with regard to the examples in FIGS. 10a-c. The substrate A being integrated in the example electrode system C as shown in FIGS. 13a-c has a number of three of the second layer(s). The first layer 1 has a width $w_1$ of 0.6 mm in the y-direction, a length $l_1$ of 0.8 mm in the x-direction and a thickness 80 μm in the z-direction. The thickness of the third layer 4 in the z-direction is 0.15 mm. The third layer 4 extending from the first layer 1 in the x-direction and in the y-direction is integrally formed with the first layer 1. Each of the second layers 2 of the example electrode system C has a length $l_2$ of 0.15 mm in the x-direction, a width of $w_2$ of 0.6 mm in the y-direction and are separated from each other by a distance of 0.15 mm in the x-direction and a thickness of 40 μm in the z-direction.

The first electrical conductive layer 3 and the second electrical conductive layer 5 are obtained from simultaneously sputtering gold in a thickness of approximately 80 nm on the second surface 1-2 of the first layer 1 and on a surface of the third layer 4, respectively, so that the second electrical conductive layer 5 is physically connected to the first electrical conductive layer 3. The sputtered electrical conductive layers 3, 5 are patterned by use of a nano-second laser so as to form two separated electrodes as shown in FIGS. 13a-c. The fourth layer 6 (passivation layer) was obtained by spin-coating the first mixture 10 onto a surface of the second electrical conductive layer 5 and curing the first mixture 10 so as to partly passivate the electrodes on the third layer 4 and to from contact pads for connecting amplification and stimulation circuitry (not shown).

As shown in FIG. 13a-c, the electrode element B (i.e. the first electrical conductive layer 3 and the substrate A) of the example electrode system C curves itself after contacting the liquid (here deionized water at room temperature) and having been swelled by the liquid including water molecules (the substrates of the electrode system examples are therefore in a saturated state in which the first and/or second layer is/are saturated by components of the liquid), such that the axis of curvature is defined in the x-direction and more precisely, is in parallel to the x-direction: FIG. 13a shows the electrode system C before folding, i.e. before submerging into liquid. The electrode system C was submerged into liquid, and FIG. 13b shows the electrode system C after 40 seconds from submerging into liquid, where the substrate A onto which the first electrical conductive layer 3 is deposited started deforming, such that the outer edge (the edge in y-direction) of the substrate A stands up in the z-direction and further approaches to the second electrical conductive layer 5 in the y-direction. FIG. 13c shows the electrode system C in a completely folded state (after 60 seconds from submerging into liquid). As shown by the examples, the first electrical conductive layer 3 forms an inner layer of the curved or folded electrode element B.

LIST OF REFERENCE SIGNS

A: substrate, B: electrode element, C: electrode system, 1: first layer, 1a: groove, 1-1: first surface, 1-2: second surface, 2: second layer, 3: first electrical conductive layer, 4: third layer, 5: second electrical conductive layer, 6: fourth layer, 10: first mixture, 20: second mixture, 70: support

The invention claimed is:

1. A substrate for an implantable microelectrode for being implanted into tissues or for being brought into contact with a single cell, in order to apply or record an electrical signal to or from the tissues or the single cell, comprising:
    a first layer; and
    a second layer deposited on at least a part of a first surface of the first layer,
    wherein each of the first layer and the second layer extends in an x-direction and in a y-direction, and the first layer and the second layer are stacked in a z-direction,
    wherein the first layer is based on a first mixture comprising:
    (a) a first photoinitiator, and
    (b) a first component comprising at least one of a first monomer, a first oligomer, or a first polymer, wherein the first monomer, the first oligomer, or the first polymer comprises a first functional group,
    wherein the first functional group is able to be activated by the first photoinitiator, so that the first component is able to be photo-polymerized through the first functional groups, and
    wherein the second layer is based on a second mixture comprising:
    (c) a second photoinitiator,
    (d) a second component comprising a second monomer, a second oligomer, or a second polymer, wherein the second monomer, the second oligomer, or the second polymer is an acid and comprises a second functional group,
    wherein the second functional group is able to be activated by the second photoinitiator, so that the second component is able to be photo-polymerized in a linear way through the second functional groups,
    (e) a base, wherein the base is able to neutralize the second monomer, the second oligomer, or the second polymer thereby forming a salt, and
    (f) a third component comprising at least one of a third oligomer or a third polymer, wherein the third oligomer or the third polymer comprises two functional groups, said two functional groups being a third functional group and a fourth functional group,
    wherein each of the third functional group and the fourth functional group is able to be activated by the second photoinitiator, so that the third component is able to cross-link the second component through the third and fourth functional groups,
    wherein a swelling capacity of the first layer is smaller than a swelling capacity of the second layer.

2. The substrate of claim 1, wherein at least one of the second, third and fourth functional groups is able to form a covalent bond with the first functional group.

3. The substrate of claim 1, wherein a ratio of the swelling capacity of the second layer to the swelling capacity of the first layer is 5 or more.

4. The substrate of claim 1, wherein the second layer entirely covers the first surface of the first layer.

5. The substrate of claim 1, wherein each of the first layer and the second layer has a length in the x-direction and a width in the y-direction, wherein the length of the second layer is shorter than the width of the second layer, and wherein the length of the second layer is shorter than the length of the first layer.

6. The substrate of claim 5, wherein the substrate comprises a plurality of the second layers deposited on the first surface of the first layer, wherein the plurality of the second layers is separated from each other in the y-direction.

7. The substrate of claim 1, wherein the length of the first layer is longer than the width of the first layer.

8. The substrate of claim 1, wherein the first layer comprises a groove formed on the first surface of the first layer or a second surface of the first layer, the second surface being opposite to the first surface in the z-direction, wherein the groove extends in the x-direction.

9. The substrate of claim 8, wherein the first layer comprises a plurality of the grooves, wherein the plurality of the grooves is separated from each other in the x-direction.

10. The substrate of claim 8, wherein the second layer at least partly penetrates into the groove.

11. The substrate of claim 8, wherein the direction of the width of the second layer and the longer direction of the groove are orthogonal to each other.

12. The substrate of claim 1, wherein the first monomer, the first oligomer, or the first polymer is a polyurethane or silicone, and wherein the first functional group is an acrylate or methacrylate group.

13. The substrate of claim 1, wherein the second component comprises the second monomer and the second monomer is acrylic acid or methacrylic acid, and wherein the second functional group is an acrylate or methacrylate group.

14. The substrate of claim 1, wherein the second component comprises a further monomer or a further oligomer, which comprises a fifth functional group, wherein the second functional group and the fifth functional group are able to be activated by the second photoinitiator, so that the second component is able to be photo-polymerized in a linear way through the second and fifth functional groups.

15. The substrate of claim 14, wherein the fifth functional group is a methacrylate group, and wherein the further monomer is hydroxyethylmethylacrylate (HEMA).

16. The substrate of claim 1, wherein the base comprises NaOH or KOH, and wherein the third oligomer or the third polymer is a polyethylene glycol, and the third functional group is an acrylate or methacrylate group, and the fourth functional group is an acrylate or methacrylate group.

17. The substrate of claim 14, wherein the molar ratio of the second monomer, the second oligomer, or the second polymer to the further monomer or the further oligomer is in a range of 1000:1 to 1:1, and wherein the molar ratio of the second monomer, the second oligomer, or the second polymer to the base is in a range of 10:1 to 10:6.

18. The substrate of claim 1, wherein the neutralization degree of the acid to the base is 10 to 60%.

19. The substrate of claim 1, wherein the molar ratio of the second component to the third component is in a range of 1000:1 to 2:1.

20. The substrate of claim 1, wherein the first mixture or the second mixture further comprises a further photoinitiator, a quencher, or a photoabsorber.

21. The substrate of claim 1, further comprising a third layer extending from the first layer in the x-direction and in the y-direction, wherein the third layer is integrally formed with the first layer, and wherein the third layer is based on the first mixture.

22. The substrate of claim 1, further comprising:
a first electrical conductive layer deposited on a second surface of the first layer, the second surface extending in the x-direction and in the y-direction and being opposite to the first surface in the z-direction,
wherein the second layer, the first layer and the first electrical conductive layer are stacked in the z-direction in this order, and
wherein the substrate is configured to be part of an electrode element for being implantable into a biological sample.

23. The substrate of claim 22, wherein the first electrical conductive layer comprises a metal film, a nanoparticle conductor, or a conductive polymer.

24. The substrate of claim 22, further comprising:
a third layer extending from the first layer in the x-direction and in the y-direction, wherein the third layer is integrally formed with the first layer, wherein the third layer is based on the first mixture, and a second electrical conductive layer deposited on the third layer, wherein the second electrical conductive layer is connected to the first electrical conductive layer,
wherein the substrate, the first electrical conductive layer, the third layer, and the second electrical conductive layer form an electrode system.

25. A method of manufacturing a substrate for an implantable microelectrode, the method comprising:
providing a first mixture comprising a first photoinitiator and a first component, the first component comprising at least one of a first monomer, a first oligomer, or a first polymer, wherein the first monomer, the first oligomer, or the first polymer comprises a first functional group;
forming a first layer by exposing the first mixture to light, wherein the first functional group is activated by the first photoinitiator, causing the first component to photo-polymerize through the first functional groups;
providing a second mixture comprising:
a second photoinitiator,
a second component comprising a second monomer, a second oligomer, or a second polymer, wherein the second monomer, the second oligomer, or the second polymer is an acid and comprises a second functional group,
a base capable of neutralizing the second monomer, the second oligomer, or the second polymer to form a salt, and
a third component comprising at least one of a third oligomer or a third polymer, wherein the third oligomer or the third polymer comprises a third functional group and a fourth functional group;
depositing the second mixture on at least a part of a first surface of the first layer; and
forming a second layer by exposing the second mixture to light, wherein the second, third, and fourth functional groups are activated by the second photoinitiator, causing the second component to photo-polymerize in a linear way through the second functional groups and the third component to cross-link the second component through the third and fourth functional groups;
wherein a swelling capacity of the first layer is smaller than a swelling capacity of the second layer.

26. The method of claim 25, wherein forming the first layer includes forming a groove on the first surface of the first layer or a second surface of the first layer, the second surface being opposite to the first surface in the z-direction, wherein the groove extends in the x-direction.

27. The method of claim 25, further comprising:
forming a first electrical conductive layer on the second surface of the first layer.

28. The method of claim 25, further comprising:
forming a first electrical conductive layer on the second surface of the first layer;
forming a third layer by exposing the first mixture to light; and
forming a second electrical conductive layer on the third layer.

29. The method of claim 25, wherein the ratio of the swelling capacity of the second layer to the swelling capacity of the first layer is 10 or more.

30. The method of claim 25, wherein the ratio of the swelling capacity of the second layer to the swelling capacity of the first layer is 20 or more.

* * * * *